United States Patent [19]

Plakas

[11] 4,013,418
[45] Mar. 22, 1977

[54] LUMINESCENT REACTION TESTING
[75] Inventor: Chris J. Plakas, Alexandria, Va.
[73] Assignee: Vitatelt Corporation, Alexandria, Va.
[22] Filed: Feb. 19, 1976
[21] Appl. No.: 659,534

Related U.S. Application Data
[63] Continuation-in-part of Ser. No. 630,943, Nov. 12, 1975.
[52] U.S. Cl. .......................... 23/253 R; 23/230 B; 195/127; 356/36; 250/361 R
[51] Int. Cl.² .................. C12K 1/10; G01N 33/16; G21H 5/00
[58] Field of Search ..................... 23/253 R, 230 B; 195/103.5 R, 127; 356/36; 250/361, 304, 364, 395, 428, 432, 483

[56] References Cited
UNITED STATES PATENTS 3,690,832  9/1972  Plakas .............................. 23/236 B
3,940,250  2/1976  Plakas et al. ..................... 23/253 R

*Primary Examiner*—Robert M. Reese
*Attorney, Agent, or Firm*—Kenneth W. Dobyns

[57] ABSTRACT

An improved apparatus for testing a sample by means of luminescent reaction to detect reactive materials therein. A ribbon of filter material, which may be translucent or opaque, is provided to filter the sample and to carry the residue to a reaction position. A translucent surface is provided to carry a reagent to the reaction position. Both surfaces are brought into mutual contact in the optical vicinity of a photodetector, which thereby detects the resulting luminescent reaction to provide an indication of the quantity of reactive material present in the sample. An improved pinion roller advances the ribbon of filter material in a reliable fashion. In an alternative embodiment, the ribbon of filter material is used without the translucent surface.

10 Claims, 8 Drawing Figures

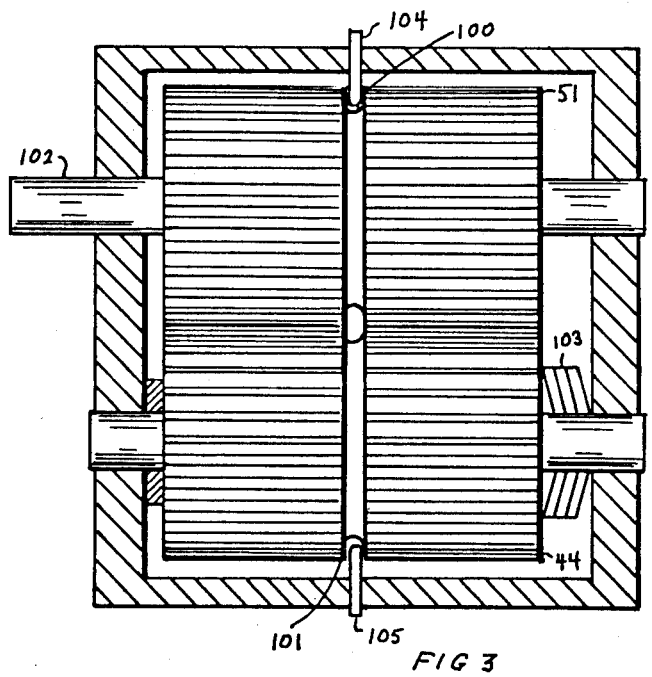
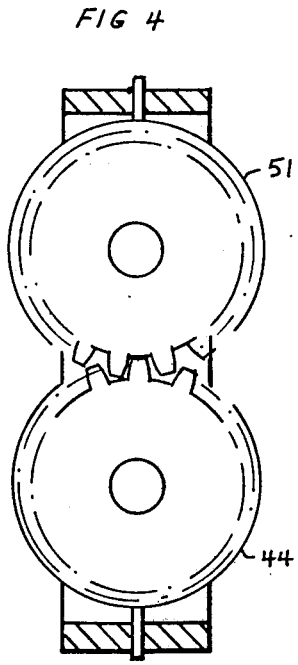
FIG 4
FIG 3
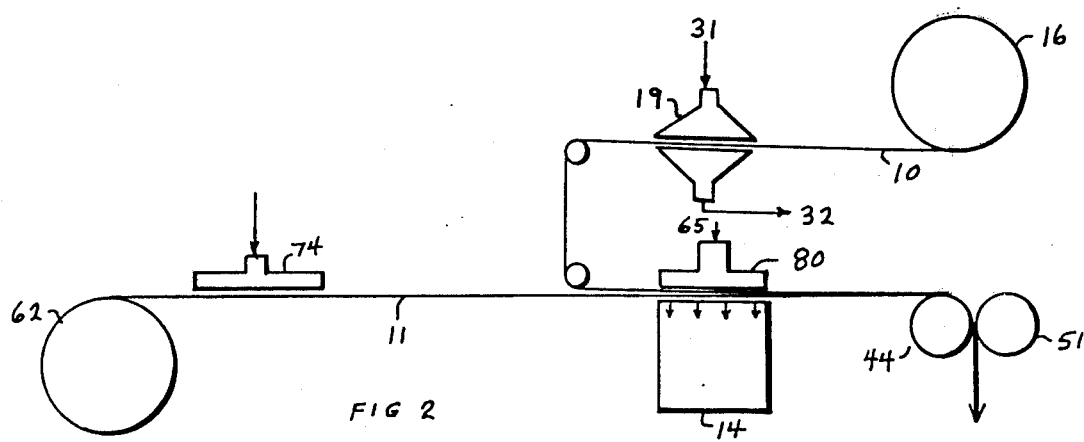
FIG 2

LUMINESCENT REACTION TESTING

This application is a continuation-in-part of copending application Ser. No. 630,943 filed Nov. 12, 1975.

CROSS REFERENCE TO RELATED APPLICATIONS

This application discloses an improvement to the invention in copending application Ser. No. 471,854, filed May 21, 1974, now U.S. Pat. No. 3,940,250, which claimed an invention in which the present inventor was a coinventor.

FIELD OF THE INVENTION

The present invention relates to a method and apparatus for detection of reactive material in a test sample and more specifically to an apparatus for detecting and measuring luminescence which occurs as a result of interaction between reactive materials and reagents.

DESCRIPTION OF THE PRIOR ART

The present invention is an improvement upon the invention in U.S. Pat. No. 3,690,832, and in copending application Ser. No. 471,854, filed May 21, 1974, about to issue as U.S. Pat. No. 3,940,250, which represent and disclose the closest known prior art.

In analytical instrumentation where tapes and films are used in wet and dry applications, the most popular tape advancing means uses rollers. However in this simple mechanism, a tape has a tendency to slip, and a positive advancement is especially difficult when two tapes are pulled together. Even more serious is the lateral drift caused by unequal friction and pressure of the two rollers along the line of contact, which forces the tapes to move sideways on the rollers.

SUMMARY OF THE INVENTION

It is therefore the object of the present invention to provide an improved device for optically detecting the reactive material in the residue of a filtered test sample concentrated on a tape filter for direct contact with reagent. One improvement relates to a single-tape machine in which the reagent is deposited directly on the ribbon or tape of filter material near the photoconductor. The single-tape machine is less expensive to operate than a two-tape machine because the cost of the translucent tape is eliminated. Another improvement relates to the use of an opaque filter in either a one-tape or two-tape system to reduce the cost and improve the versatility of the system.

BRIEF DESCRIPTION OF THE DRAWINGS

FIG. 2 is a schematic diagram of a device similar to the device in FIG. 1, but using two pinion rollers to advance the two ribbons or tapes.

FIG. 3 is a cross-sectional view of a pinion roller means for use in the embodiment of FIGS. 1, 2 or 5 for moving ribbons of filter material through the device.

FIG. 4 is another view of the pinion roller means of FIG. 3.

DESCRIPTION OF THE PREFERRED EMBODIMENTS

Figure 1:
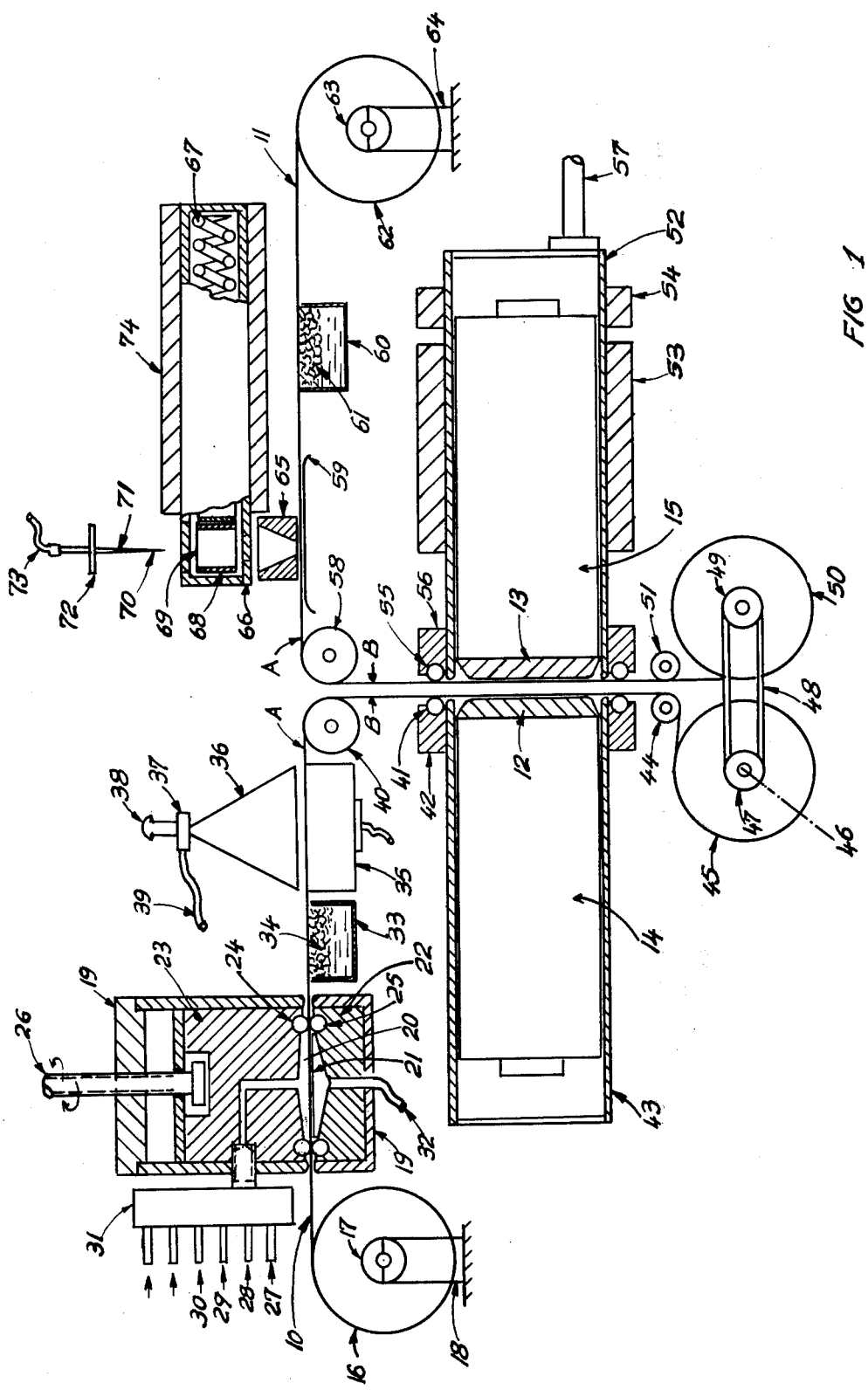
FIG. 1 is a schematic diagram of a surface reaction apparatus according to the prior copending application and illustrating the principles of operation according to the prior invention.

Referring now to FIG. 1 of the drawings, for detection of bioluminescent reaction with the device of the prior invention, translucent ribbon of filter material 10 providing a first carrier element begins its motion from a supply reel 16, passes through a sample filtration unit 19 where sample-containing reactive materials are forced through the filter, then advances between the extractors 35 and 36 and carries the residue between the photodetectors 14 and 15 for reaction. A translucent film or surface 11 providing a second carrier element begins its linear motion from a supply reel 62, passes under a reagent feeder 65, and carries the reagent in the form of an aquatic layer between the photodetectors 14 and 15. Face A of filter 10 bearing reactive material and face A of surface or film 11 bearing the reagent are drawn together between the photodetectors 14 and 15. As the reagent medium and reactive material contact each other, a reaction occurs, and the resulting luminescence is transmitted to the photodetectors through the translucent films via coupling liquid and light pipes.

For more specific reference to the operation of the system for bioluminescent and the chemiluminescent detection, reference is made to prior copending application Ser. No. 471,854, which is incorporated by reference herein.

Filter film 10 for use in the device of FIG. 1 may be made of cellulose or other plastic translucent materials. Also, materials that become translucent or transparent when their pores are filled with samples or liquids of the same refractive index may be used effectively. The thickness of the material should be between 50 microns and 500 microns for greatest effectiveness, although other thicknesses may be used.

Filter film 10 travels over a guiding roller 40 and then between photodetectors 14 and 15. After leaving the photodetector region, the filter film 10 continues its motion around a guiding roller 44 and is collected on a storage reel 45 which is operated through an extension shaft 46.

Film 11, carrying the reagents, passes over a guide roller 58 and brings the reagent between the photodetectors 14 and 15 for the reaction process. After the reaction is completed, the film 11 passes over a guide roller 51 and is collected on a storage reel 50.

A translucent film for this system to provide the translucent surface may be made of cellulose, such as cellophane, or other suitable material, and can be obtained commercially from Dupont and other manufacturers. A translucent filter material can be made of the same materials, and can also be obtained commercially from Gelmar Instrument Co. of Ann Arbor, Michigan, or other manufacturers of filter materials. Opaque filters are widely available.

FIG. 2 is a schematic drawing of another surface reaction device in which the same numerals are used in the drawings to present the same parts as in FIG. 1.

Referring now to FIG. 2, the filter film 10 begins its motion from the supply reel 16, passes through a sample filtration unit 19, where sample-containing reactive material is forced through the filter. When the filtration process is completed, extractant liquid is introduced into the filtration unit through the supply entrance 31. Filtrate and other waste liquids are discharged through the opening 32. When extraction is completed, pinion rollers 44 and 51 pull the film and bring the portion of the filter carrying the reactive material to reaction position between the plate 80 and the photodetector 14. The reagent material is injected on the filter from the inlet 65. The reagent saturates the filter carrying reactive material. The emitted luminescence is detected by the photodetector 14. The filter film 10 may be of any commercially available filter film material of desirable mean pore size, and may be opaque to light or translucent.

Pulled by pinion rollers 44 and 51, translucent film 11 begins its linear motion from a supply reel 62, passes under the reagent supply plate 74 and continues its motion between plate 80 and photodetector 14. The translucent film 11 serves to prevent contamination of the photodetector window by the reaction medium and to carry the reagent or extractant from the supply plate 74 to reaction position.

An advantage of the system of FIG. 2 over that of FIG. 1 is that opaque filter material can be used in the system of FIG. 2. Since the residue is deposited on the side of filter tape 10 which is later positioned adjacent to the photodetector 14, the filter tape does not need to be transparent or translucent. The reagent may be deposited on the opposite side from the residue, because it soaks through to the residue. The film 11, if used, must still be translucent.

Figure 5:
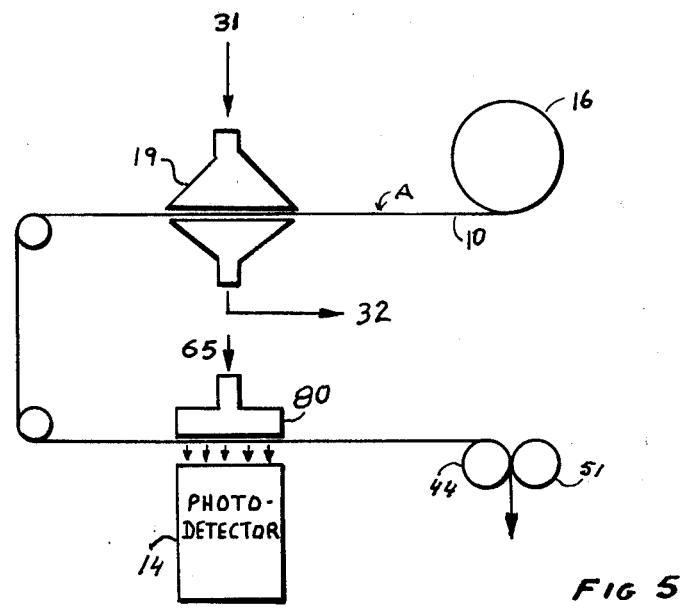
FIG. 5 is a schematic diagram of a device which is similar to FIG. 2, but which omits the transparent ribbon and deposits the reagent directly on the filter tape.
Figure 6:
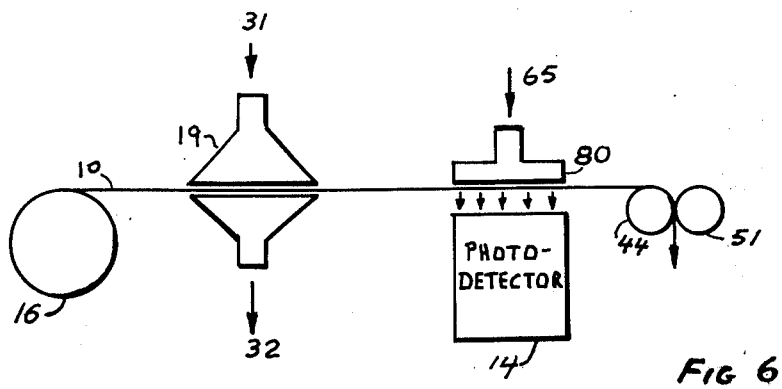
FIG. 6 is a schematic diagram of a device which is similar to FIG. 5, but in which the reagent is deposited on the same side of the filter as the residue.
Figure 7:
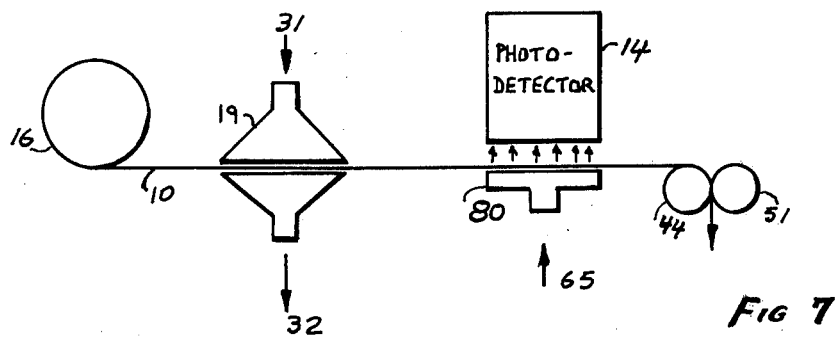
FIG. 7 is a schematic diagram of a device which is similar to FIG. 6 except that the photodetector and reagent dispenser are in reversed positions.

The apparatus of FIG. 2 may be operated with only filter tape 10 as illustrated in FIG. 5. In this operation, plate 80 is raised a distance above photodetector 14 to insure that the photodetector window is not contaminated with residuals of the reaction material. In single tape operation, filtration and extraction take place in the filtration unit 19. Liquid reagent material is injected through the opening 65 of a liquid reagent dispenser to saturate the filter portion which carries the reactive material on face A, thus insuring against contamination of the plate 80. FIG. 6 is an alternative embodiment of FIG. 5 in which the residue is deposited on the same side of the filter tape as is the reagent.

The instrument design provides several alternative methods for applying extractants and reagents. Extraction may take place in the filtration unit where extraction liquids such as methylene chloride ($CH_2Cl_2$) may be forced through the sample-carrying filter film. Since methylene chloride ruptures bacterial cells but does not dissolve reactive material extracted from cells, the reactive material remains on face A of the filter film 10. Other liquid extractants may be dropped in small volumes on film 10 through inlet 31. Another method is to apply extraction liquid to face A of film 11 through inlet 74, said film coming into contact with sample of face A of film 10 under plate 80. After extraction time is allowed, reagent is injected through inlet 65. When reagent injection is made through inlet 65 the plate 80 is in fixed position and the films 10 and 11 are in continuous contact. When reagent injection is made through inlet 74, the plate 80 is actuated downward to bring films 10 carrying reactive material and 11 carrying reagent material into contact.

Another alternative method involves supplying extraction material through inlet 65 and reagent material through inlet 74, in which case plate 80 is manually actuated to bring films 10 and 11 into contact.

When reagent is supplied through element 65, the extractant can be supplied either through element 74 or 31, with sample filtration through element 31. When the reagent is supplied through element 74, the extractant can be supplied either through element 31 or 65, with sample filtration through element 31.

In chemiluminescence and bioluminescence techniques the detection of bacteria is achieved by rupturing the bacterial cells with extractant material, thus releasing reactive material, mixing it with reagents, and detecting and recording the amount of luminescence emitted as a result of the interaction between reactive material and reagents. Extractant liquids which do not dissolve reactive materials may be forced through the filter after sample filtration is completed. In this case bacterial cells are ruptured and the reactive material remains on the filter. For example, methylene chloride $CH_2Cl_2$ does not dissolve ATP reactive material and may be used successfully. Generally methylene chloride does not dissolve or mix with other materials. However it will mix with dioctyl sodium sulfosuccinate, which is another excellent extractant. Other liquid extractants which dissolve extracted reactive materials, such as nitric acid $HNO_3$, may be used in very small quantities on the filter area which carries bacterial cells.

FIGS. 3 and 4 show the construction of the guide rollers 44 and 51 as pinion rollers. The driver pinion 51 may be rotated by manual or electromechanical means through the extended shaft 102, and in turn, pinion 51 rotates the driven pinion 44. The selected pitch of the teeth of the pinions depends on the thickness of the tapes or film and should be wide enough to achieve bending of the film between the teeth. Both pinions are machined to permit pins 104 and 105 to enter respective circumferential channels 100 and 101 thereby preventing films from wrapping back around the pinions. A spring washer 103 functions as a clutch to exercise a pressure on the pinion 44 in such a way that pinion 51 encounters resistance between its teeth in the direction of the pressure angle of the pinion, thus trapping the film along the teeth at the pitch circle and advancing it.

The distance between the axes of the pinions 44 and 51 is larger than the normal center distance of regular gears in order to permit a backlash or play larger than the thickness of the films passing through them. When the pinions are not in motion, the driver pinion is free of any force and thus frees the films allowing them to recover from any lateral displacement tension.

Although pinion 51 is shown as the driving roller and pinion 44 as the driven roller, this relationship is equally suitable when reversed. The pinion rollers 51 and 44 may be made of plastic or metal and are available as "wire pinions" in any length from gear manufacturers.

Dioctyl sodium sulfosuccinate is an excellent extraction medium. Besides the ability to rupture biological cells, it drops the surface tension of the liquid, thus permitting a small amount of extraction volume to saturate the whole area of the filter surface. Only a small amount of extraction liquid is required on the filter in order to prevent reagent material loss.

The dioctyl sodium sulfosuccinate as used, is diluted in concentration to approximately 5% in distilled water.

Figure 8:
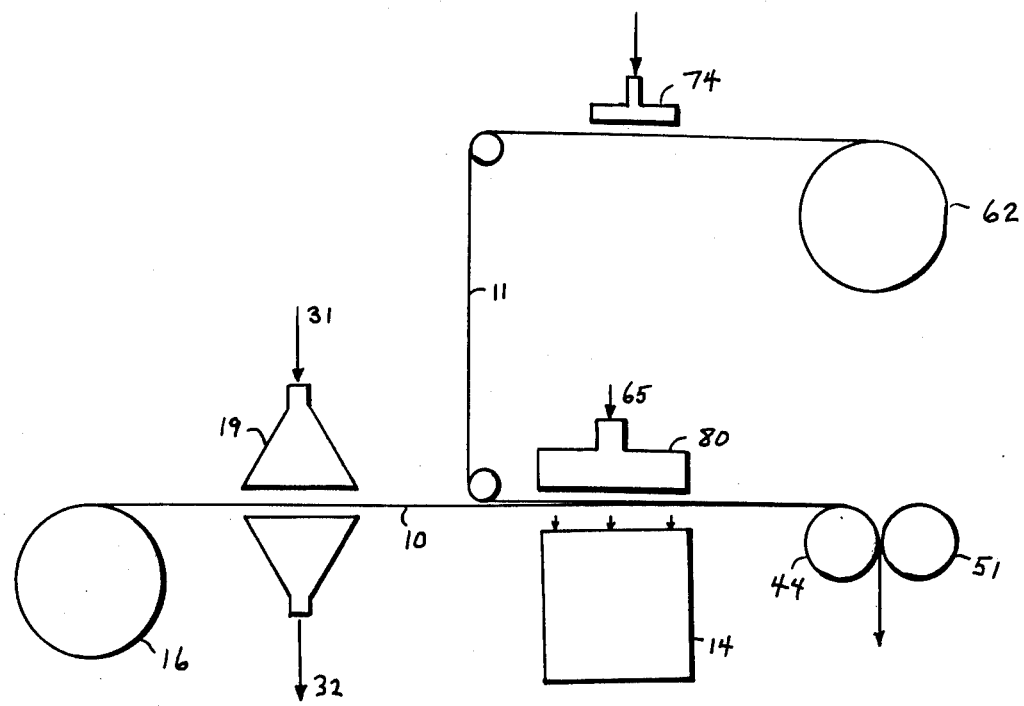
FIG. 8 is a schematic diagram of a device which is similar to FIG. 2, but reverses the positions of the two tapes with respect to the photodetector.

In FIG. 8, a system similar to FIG. 2 is illustrated except that the positions of the filter ribbon and the reagent tape are reversed with respect to the photodetector. This arrangement allows the use of an opaque reagent tape 11 with a transparent filter ribbon 10.

The chemiluminescence method of detecting bacterial cells is based on microbial activation of the oxidation of the luminol monoanion by perborate in the presence of iron porphyrins contained in microorganisms. Hydrogen peroxide or other chemicals may be used instead of perborate.

In chemiluminescence, separate lysing (cell breaking) and extraction steps are not required. By mixing extractant with reagent, the testing operation is simplified.

What is claimed is:

1. A surface reaction system for detecting biological cells as reactive materials in a test sample containing a plurality of biological cells by means of luminescent reaction, comprising:
   A. filtering means for filtering said sample through an elongated ribbon of filter material to produce a residue on the ribbon containing biological cells from the sample,
   B. extraction means operatively associated with the ribbon for rupturing the cells in the residue while on said ribbon of filter material,
   C. advancing means coacting with the ribbon for advancing a portion of the ribbon of filter material containing the residue to a new position,
   D. liquid dispenser means for depositing liquid reagent directly on said portion of the ribbon of filter material containing the residue while said portion is in said new position, and
   E. photodetector means in optical proximity to the ribbon for detecting the intensity of a luminescent reaction which occurs when the reagent and the ruptured cells in the residue react together.

2. A system according to claim 1 wherein the filtering means and the liquid dispenser means further comprise means for depositing the residue and the reagent on opposite sides of the filter material.

3. A system according to claim 1 wherein the filtering means and the liquid dispensing means further comprise means for depositing the residue and the reagent on the same side of the filter material.

4. A system according to claim 1 wherein the photodetector is located to detect the luminescent reaction while said portion is in said new position.

5. A system according to claim 1, wherein the extraction means comprises means for dispensing, as a liquid extractant, a solution of about 5% dioctyl sodium sulfosuccinate in distilled water.

6. A system according to claim 1 wherein the filter material is light transmitting.

7. A system according to claim 1 wherein the filter material is opaque.

8. A system according to claim 1 wherein the extraction means is an extractant material dispensed with the liquid reagent.

9. A surface reaction system for detecting biological cells as reactive materials in a test sample containing a plurality of biological cells by means of luminescent reaction, comprising:
   A. filtering means for filtering said sample through an elongated ribbon of opaque filter material to produce a residue on the ribbon containing biological cells from the sample on one side of the filter material,
   B. extraction means operatively associated with the ribbon for rupturing the cells in the residue while on said ribbon of filter material,
   C. an elongated tape of translucent material having a portion thereof positioned adjacent to the side of the ribbon of filter material on which said residue is deposited,
   D. advancing means coating with the ribbon and the tape for simultaneously advancing the ribbon and the tape,
   E. means for bringing reagent material into contact with the residue on the ribbon, and
   F. photodetector means situated in optical proximity to the ribbon and the tape on the side of the ribbon of opaque filter material on which the residue is deposited and separated from the residue by the tape of translucent material for detecting the luminescent reaction which occurs when the reagent and the ruptured cells in the residue react together.

10. A surface reaction system for detecting biological cells as reactive materials in a test sample containing a plurality of biological cells by means of luminescent reaction, comprising:
   A. filtering means for filtering said sample through an elongated ribbon of translucent filter material to produce a residue on the ribbon containing biological cells from the sample on one side of the filter material,
   B. extraction means operatively associated with the ribbon for rupturing the cells in the residue while on said ribbon of filter material,
   C. an elongated tape of opaque material having a portion thereof positioned adjacent to the side of the ribbon of filter material on which said residue is deposited,
   D. advancing means coating with the ribbon and the tape for simultaneously advancing the ribbon and the tape,
   E. means for bringing reagent material into contact with the residue on the ribbon, and
   F. photodetector means situated in optical proximity to the ribbon and the tape on the side of the ribbon of translucent filter material away from said one side on which the residue is deposited and separated from the residue by the ribbon of translucent filter material for detecting the luminescent reaction which occurs when the reagent and the ruptured cells in the residue react together.

* * * * *